United States Patent
Sah et al.

(10) Patent No.: US 9,035,780 B2
(45) Date of Patent: May 19, 2015

(54) APPARATUS FOR PREVENTING PASSIVE TASK-RELATED FATIGUE OF DRIVER AND METHOD THEREOF

(71) Applicant: Hyundai Motor Company, Seoul (KR)

(72) Inventors: Sung Jin Sah, Gyeonggi-do (KR); Sung Min Park, Seoul (KR); Hui Sung Lee, Gyeonggi-do (KR); Kwang Myung Oh, Daejeon (KR)

(73) Assignee: Hyundai Motor Company, Seoul (KR)

( * ) Notice: Subject to any disclaimer, the term of this patent is extended or adjusted under 35 U.S.C. 154(b) by 31 days.

(21) Appl. No.: 14/067,163

(22) Filed: Oct. 30, 2013

(65) Prior Publication Data

US 2015/0002298 A1     Jan. 1, 2015

(51) Int. Cl.
| | |
|---|---|
| G08B 23/00 | (2006.01) |
| G08B 21/06 | (2006.01) |
| B60K 28/10 | (2006.01) |
| A61B 5/11 | (2006.01) |
| B60K 28/06 | (2006.01) |

(52) U.S. Cl.
CPC ............... *G08B 21/06* (2013.01); *B60K 28/10* (2013.01); *A61B 5/1116* (2013.01); *B60K 28/066* (2013.01)

(58) Field of Classification Search
CPC ...... G08B 21/06; B60K 28/10; B60K 28/066; A61B 5/1116
USPC ................... 340/576, 573.7, 575, 573.1, 441, 340/988–900; 600/383; 180/272
See application file for complete search history.

(56) References Cited

U.S. PATENT DOCUMENTS

| | | | | |
|---|---|---|---|---|
| 7,124,027 | B1 * | 10/2006 | Ernst | 701/301 |
| 7,301,464 | B2 * | 11/2007 | Coulter | 340/573.7 |
| 8,022,831 | B1 * | 9/2011 | Wood-Eyre | 340/575 |
| 2002/0198632 | A1 * | 12/2002 | Breed et al. | 701/1 |
| 2006/0267781 | A1 * | 11/2006 | Coulter | 340/573.7 |
| 2008/0071547 | A1 * | 3/2008 | Prieto et al. | 704/275 |
| 2008/0231461 | A1 * | 9/2008 | Sanchez et al. | 340/575 |
| 2008/0291032 | A1 * | 11/2008 | Prokhorov et al. | 340/576 |
| 2010/0102972 | A1 * | 4/2010 | Middlekauff et al. | 340/576 |
| 2013/0131907 | A1 * | 5/2013 | Green et al. | 701/23 |
| 2013/0207804 | A1 * | 8/2013 | Li et al. | 340/575 |
| 2013/0257620 | A1 * | 10/2013 | Tsou et al. | 340/573.1 |
| 2014/0139341 | A1 * | 5/2014 | Green et al. | 340/576 |
| 2014/0167948 | A1 * | 6/2014 | Mejia | 340/441 |
| 2014/0240132 | A1 * | 8/2014 | Bychkov | 340/576 |
| 2014/0276090 | A1 * | 9/2014 | Breed | 600/473 |
| 2015/0002298 | A1 * | 1/2015 | Sah et al. | 340/576 |
| 2015/0005608 | A1 * | 1/2015 | Evans et al. | 600/383 |

FOREIGN PATENT DOCUMENTS

| | | |
|---|---|---|
| JP | S63-148530 | 9/1988 |
| JP | 2003-240562 | 8/2003 |
| JP | 2007164366 A | 6/2007 |

(Continued)

*Primary Examiner* — Hoi Lau
(74) *Attorney, Agent, or Firm* — Mintz Levin Cohn Ferris Glovsky and Popeo, P.C.; Peter F. Corless

(57) ABSTRACT

A device that causes a driver not to feel passive task-related fatigue by performing interaction with the driver at a time when the driver feeling passive task-related fatigue, thereby promoting safe driving. In particular, phrase "the interaction with the driver" refers to a series of operations viewing quiz data or beat sequence data to the driver, receiving a response, and visually, acoustically, and tactilely informing a result according to the response, and a control of each component for the operation.

9 Claims, 3 Drawing Sheets

(56) References Cited

FOREIGN PATENT DOCUMENTS

| KR | 10-1998-030211 | 7/1998 |
| KR | 10-1998-048428 | 9/1998 |
| KR | 10-1999-0084391 | 12/1999 |
| KR | 10-2003-0094564 | 12/2003 |

* cited by examiner

APPARATUS FOR PREVENTING PASSIVE TASK-RELATED FATIGUE OF DRIVER AND METHOD THEREOF

CROSS-REFERENCE TO RELATED APPLICATION

This application is based on and claims priority from Korean Patent Application No. 10-2013-0073765, filed on Jun. 26, 2013 in the Korean Intellectual Property Office, the disclosure of which is incorporated herein in its entirety by reference.

BACKGROUND OF THE INVENTION

1. Field of the invention

The present invention relates to an apparatus for preventing passive task-related fatigue of a driver and a method thereof, and more particularly, to a technology causing the driver not to feel passive task-related fatigue by performing an interaction with the driver at a time when the driver is feeling the passive task-related fatigue, thereby promoting safe driving.

In particular, the phrase "an interaction with the driver" means a series of operations viewing quiz data or beat sequence data to the driver, receiving an answer, and visually, acoustically, and tactilely informing a result according to the answer, and a control of each component for the operation.

2. Description of the Prior Art

In general, technologies that prevent drowsy driving by the driver typically sense whether or not the driver is drowsy by analyzing a specific motion of the driver by installing a camera for monitoring the driver within a vehicle. Here, the specific motion includes motions such as a motion that the driver yawns, a motion that the driver abnormally blinks his/her eyes, a motion that the driver frequently nods his/her head, and/or the like. As such, when drowsiness of the driver is identified, an alarm is generally sounded in order to waken the driver or stop the vehicle.

However, these means of alerting the driver are very inefficient because these methods are aimed awakening the driver who is already entered into a drowsy state. As many of us know, once an individual is in a drowsy state it is hard to get out of that drowsiness state. For example, a driver who yawns many times, has an eyelid partly closed, or frequently nods his/her head is likely to continue to perform these actions even after an alarm has been sounded.

Typically, the drowsiness of the driver may be divided into a step of sensing passive task-related fatigue, which is an initial step, a step of entering sleep, and a sleeping step. In this case, the passive task-related fatigue is disclosed in detail in "Driver fatigue: The importance of identifying causal factors of fatigue when considering detection and countermeasure technologies" described in "Transportation Research Part F 12 (2009) 218-224" by Jennifer F. May, Carryl L. Baldwin" which is hereby incorporated by reference.

The steps of entering a sleepy state occurs when the driver yawns many times, has an eyelid partly closed, or frequently nods his/her head, and in this step, it is difficult to arouse the driver from the sleepy state. Therefore, a demand for a technology capable of preventing the passive task-related fatigue which is the initial step of drowsiness in advance, that is, the fatigue generated by only keeping eyes forward without any manipulation by the driver while driving has increased.

SUMMARY OF THE INVENTION

Accordingly, the present invention has been made to solve the above-mentioned problems occurring in the prior art while advantages achieved by the prior art are maintained intact. One aspect is to provide an apparatus for preventing passive task-related fatigue of a driver and a method thereof causing the driver not to feel the passive task-related fatigue by performing interaction with the driver at the time when the driver feels the passive task-related fatigue, thereby promoting safe driving.

Objects of the present invention are not limited the above-mentioned subject, other objects and advantages of the present invention which are not mentioned can be appreciated by the following description and will be clearly described by exemplary embodiments of the present invention. In addition, it will be easily known that the objects and advantages of the present invention can be implemented by means and a combination thereof shown in the appended claims.

In one aspect of the present invention, there is provided an apparatus for preventing passive task-related fatigue of a driver, the apparatus including: a cruise control monitor that monitors an on or off state of a cruise control switch mounted in a vehicle; a receiver that receives quiz data corresponding to a position of the vehicle from a server; a display that displays the quiz data received by the receiver; an interface that receives an answer for a quiz from the driver; an audio device that outputs a sound corresponding to the answer from the driver received through the interface; a sheet vibrator vibrating a sheet when the answer from the driver is a wrong answer; and a controller performing an interaction with the driver based on the quiz data corresponding to the position of the vehicle received through the receiver when the on state of the cruise control switch is maintained longer than a threshold time.

In another aspect of the present invention, there is provided a method for preventing passive task-related fatigue of a driver, the method including: detecting, by a cruise control monitor, an on state of a cruise control switch mounted in a vehicle; counting, by a controller, whether the on state of the cruise control switch exceeds a threshold time; receiving, by a receiver, quiz data corresponding to a position of the vehicle from a server under control of the controller when the on state of the cruise control switch exceeds a threshold time; and performing, by the controller, an interaction with the driver based on the quiz data corresponding to the position of the vehicle received through the receiver.

In still another aspect of the present invention, there is provided a method for preventing passive task-related fatigue of a driver, the method including: detecting, by a cruise control monitor, an on state of a cruise control switch mounted in a vehicle; counting, by a controller, whether the on state of the cruise control switch exceeds a threshold time; monitoring, by a steering wheel monitor, a manipulating amount of a steering wheel of the vehicle; receiving, by a receiver, quiz data corresponding to a position of the vehicle from a server under control of the controller when the manipulating amount of the steering wheel exceeds a threshold value in a state in which the on state of the cruise control switch does not exceed the threshold time; and performing, by the controller, an interaction with the driver based on the quiz data corresponding to the position of the vehicle received through the receiver.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
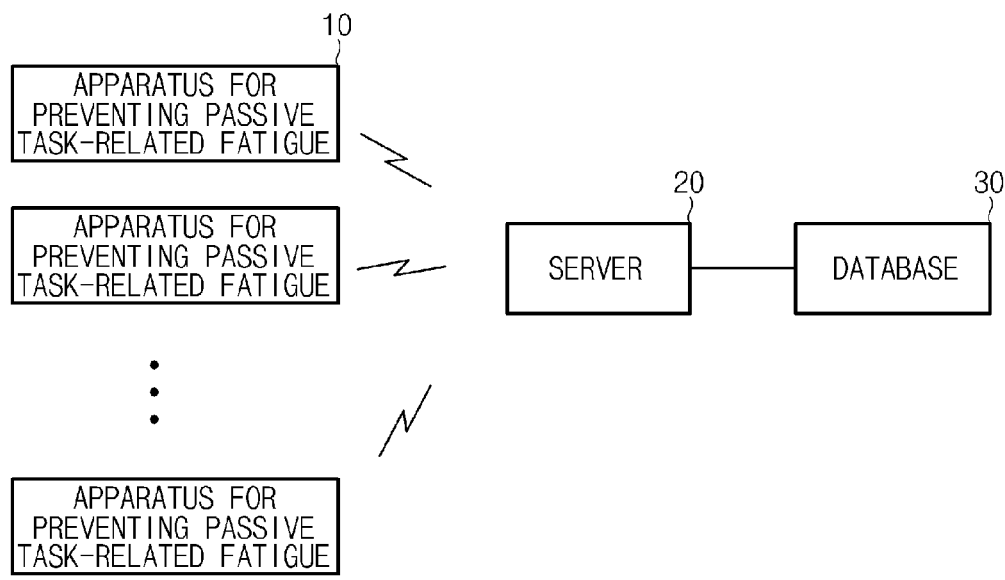
FIG. 1 is a configuration diagram of a system for preventing passive task-related fatigue of a driver according to an exemplary embodiment of the present invention.

The above objects, features, and advantages will be apparent by a detail description described below in detail with reference to the accompanying drawings and therefore, the technical ideas of the present invention can be easily practiced by a person with ordinary skill in the art to which the present invention pertains. In addition, in describing the present invention, when a detailed description of well-known technology relating to the present invention may unnecessarily obscure the spirit of the present invention, a detailed description thereof will be omitted. Hereinafter, exemplary embodiments of the present invention will be described in detail with reference to the accompanying drawings.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles, fuel cell vehicles, and other alternative fuel vehicles (e.g. fuels derived from resources other than petroleum).

Additionally, it is understood that the below methods are executed by at least one controller. The term controller refers to a hardware device that includes a memory and a processor configured to execute one or more steps that should be interpreted as its algorithmic structure. The memory is configured to store algorithmic steps and the processor is specifically configured to execute said algorithmic steps to perform one or more processes which are described further below.

Furthermore, the control logic of the present invention may be embodied as non-transitory computer readable media on a computer readable medium containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

FIG. 1 is a configuration diagram of a system for preventing passive task-related fatigue of a driver according to an exemplary embodiment of the present invention. As shown in FIG. 1, the system for preventing the passive task-related fatigue of the driver to which the exemplary embodiment of the present invention is applied includes one or more apparatuses 10 for preventing passive task-related fatigue, a server 20, and a database 30.

First, the apparatus 10 for preventing the passive task-related fatigue mounted in each vehicle inter-works with the server 20 and prevents the passive task-related fatigue of the driver based on various data received from the server 20. Here, various data include quiz data related to a current position of the driver and beat sequence data associated with various music.

For example, the quiz data, which is a selective type of quiz data of YES or NO, may include questions such as "A river currently flows on the left", "Baseball park is currently on the right", "A bridge is currently ahead", or the like. In this case, the driver may answer each question by directly seeing with his/her own eyes. Further, the server 20 receives current position information from the vehicle to provide the quiz data corresponding to the position of the vehicle to the vehicle in real time.

Particularly, the apparatus 10 for preventing the passive task-related fatigue monitors on or off of a cruise control switch in order to detect the timing when the driver feels the passive task-related fatigue. That is, the apparatus 10 for preventing the passive task-related fatigue determines when an on state of the cruise control switch exceeds a threshold time as the timing when the driver is most likely to feel the passive task-related fatigue. That is, when an operation time of a cruise control exceeds the threshold time, the apparatus 10 for preventing the passive task-related fatigue determines the passive task-related fatigue.

In this case, the cruise control, which is a constant speed control apparatus, is an apparatus for driving while maintaining a constant speed without stepping on the accelerator once the speed is set by the driver. In addition, the threshold time, which is an average value obtained through experimental data targeted for a plurality of drivers for each of a plurality of various times (8:00 AM, 2:0 PM, 6:00 PM, and the like), is preferably 7 minutes, as an example.

According to another exemplary embodiment of the present invention, the apparatus 10 for preventing the passive task-related fatigue may further include a steering wheel monitor (not shown) which is configured to detect when the driver feels the passive task-related fatigue.

For example, the apparatus 10 for preventing the passive task-related fatigue determines that the driver is feeling passive task-related fatigue, when a manipulated amount of the steering wheel is suddenly and rapidly increased even though the on state of the cruise control switch has not exceeded the threshold time. In this case, the manipulating amount of the steering wheel refers to an amount that the steering wheel is rotated.

Meanwhile, the apparatus 10 for preventing the passive task-related fatigue requests the quiz data or the beat sequence data from the server 20 according to information set by the driver. In this case, when the driver does not specifically select the data, the quiz data which is set as a default is requested.

Next, the server 20 inter-works with the apparatus 10 for preventing the passive task-related fatigue mounted in each vehicle to obtain position information of each vehicle and provide the quiz data or the beat sequence data according to a request from each apparatus 10 for preventing the passive task-related fatigue. In this case, the server 20 selectively provides the quiz data corresponding to the position information of each vehicle. The database 30 then stores the quiz data corresponding to each position and the beat sequence associated with various music.

Figure 2:
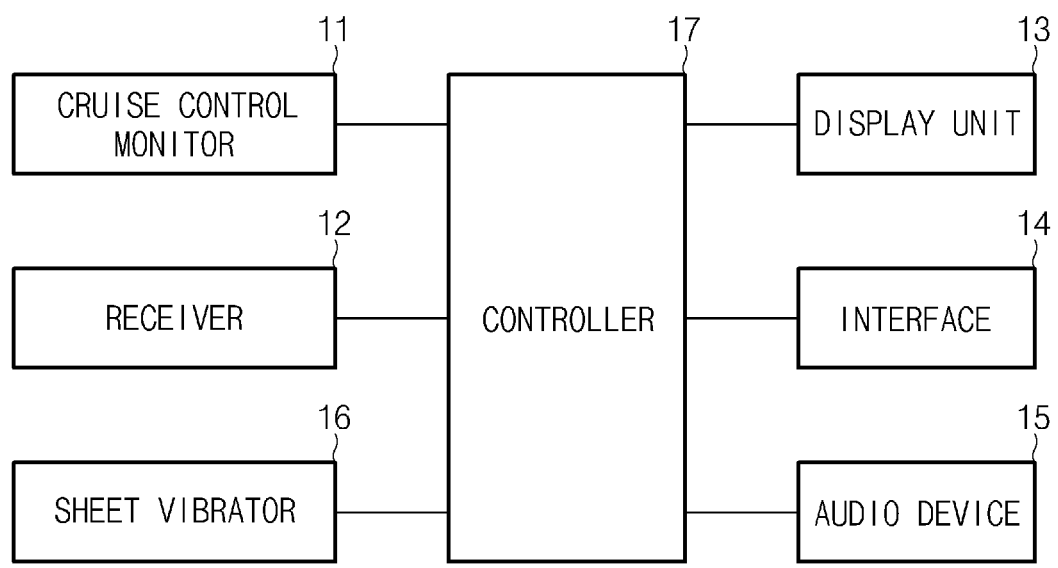
FIG. 2 is a configuration diagram of an apparatus for preventing passive task-related fatigue of a driver according to an exemplary embodiment of the present invention.

FIG. 2 is a configuration diagram of an apparatus for preventing passive task-related fatigue of a driver according to an exemplary embodiment of the present invention. As shown in FIG. 2, the apparatus for preventing the passive task-related fatigue of the driver includes a cruise control monitor 11, a receiver 12, a display unit 13, an interface 14, an audio device 15, a sheet vibrator 16, and a controller 17. Describing the respective components, first, the cruise control monitor 11 monitors an on or off state of the cruise control switch for operating the cruise control mounted in the vehicle.

Next, the receiver 12 inter-works with the server 20 to provide the position information of the vehicle and receives the quiz data corresponding to the position of the vehicle from the server 20. The display unit 13, which is a head up display (HUD), as an example, displays the quiz received by the receiver 12. In addition, the display unit 13 may display the beat sequence.

The interface 14, which is a touch pad mounted on the steering wheel of the vehicle, receives an answer for the quiz from the driver. In addition, the interface 14 may receive beat from the driver. The audio device 15 outputs a sound informing the driver of a correct answer when an answer from the driver received through the interface 14 is the correct answer and outputs a sound informing the driver of a wrong answer when the answer from the driver is the wrong answer, under control of the controller 17. In addition, the audio device 15 may output various music is some exemplary embodiments of the present invention.

Furthermore, the sheet vibrator 16 prevents the passive task-related fatigue of the driver by vibrating a sheet when the answer from the driver received through the interface 14 is the wrong answer, under control of the controller 17. The controller 17 controls the respective components accordingly. Particularly, the controller 17 may monitor whether the time that the cruise control switch has been in an on position has exceed the threshold time by checking the on state of the cruise control switch through the cruise control monitor 11.

In this case, when the on state of the cruise control switch is maintained beyond the threshold, the controller 17 immediately provides the current position information to the server 20 through the receiver 12 and receives quiz data corresponding to the position from the server 20 to perform an interaction with the driver. In addition, the controller 17 may periodically provide the position information of the vehicle through the receiver 12.

Figure 3:
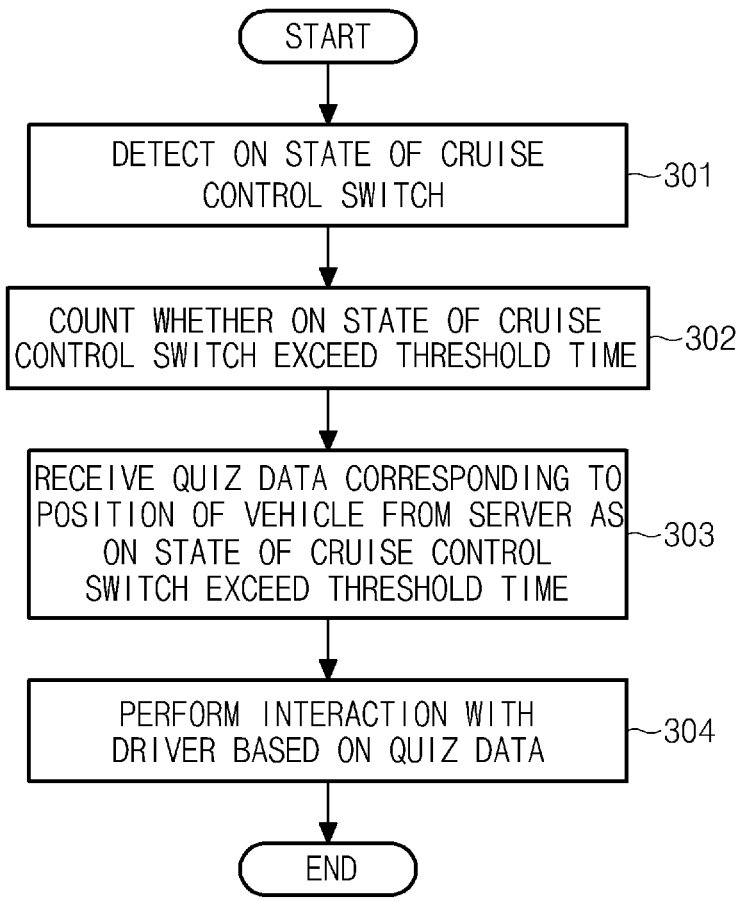
FIG. 3 is a flow chart of a method for preventing passive task-related fatigue of a driver according to an exemplary embodiment of the present invention.

FIG. 3 is a flow chart of a method for preventing passive task-related fatigue of a driver according to an exemplary embodiment of the present invention. First, the cruise control monitor 11 detects the on state of the cruise control switch mounted in the vehicle (301). Next, the controller 17 determines whether the on state of the cruise control switch has exceeded the threshold time (302). When the on state of the cruise control switch exceeds the threshold time, the receiver 12 receives the quiz data corresponding to the position of the vehicle from the server 20 under control of the controller 17 (303), and the controller 17 performs the interaction with the driver based on the quiz data corresponding to the position of the vehicle received through the receiver 12 (304).

Furthermore, in some instances, even when the on state of the cruise control switch has not exceeded the threshold time, when an amount a steering wheel is manipulated exceeds a threshold value, the controller 17 may perform the interaction with the driver based on the quiz data corresponding to the position of the vehicle received through the receiver 12.

In the present invention, the phrase "an interaction with the driver" means a series of operations viewing quiz data or beat sequence data to the driver, receiving an answer, and visually, acoustically, and tactilely informing a result according to the answer, and a control of each component for the operation.

As stated above, the method according to the exemplary embodiment of the present invention as described above may be written with a computer program. Codes and code segments configuring the computer program may be easily deduced by computer programmers in the art. In addition, the written computer program is stored in computer readable recording media (information storage media) and is read and executed by computers, thereby implementing the methods according to the present invention. In addition, the recording media includes all types of recording media capable of being read by the computer.

As set forth above, according to the exemplary embodiment of the present invention, the safe driving may cause the driver not to feel the passive task-related fatigue by performing interaction with the driver at the time when the driver feels the passive task-related fatigue, thereby promoting safe driving.

The present invention described above may be variously substituted, altered, and modified by those skilled in the art to which the present invention pertains without departing from the scope and spirit of the present invention. Therefore, the present invention is not limited to the above-mentioned exemplary embodiments and the accompanying drawings.

What is claimed is:

1. An apparatus for preventing passive task-related fatigue of a driver, the apparatus comprising:
   a cruise control monitor that monitors an on or off state of a cruise control switch mounted in a vehicle;
   a receiver that receives quiz data corresponding to a position of the vehicle from a server;
   a display that displays the quiz data received by the receiver;
   an interface that receives an answer for the quiz data from the driver;
   an audio device that outputs a sound corresponding to the answer from the driver received through the interface;
   a sheet vibrator that vibrates a sheet when the answer from the driver is a wrong answer; and
   a controller configured to perform an interaction with the driver based on the quiz data corresponding to the position of the vehicle received through the receiver when the on state of the cruise control switch has been maintained beyond a threshold time.

2. The apparatus for preventing passive task-related fatigue of a driver according to claim 1, further comprising a steering wheel monitor that monitors an amount that a steering wheel of the vehicle is manipulated.

3. The apparatus for preventing passive task-related fatigue of a driver according to claim 2, wherein the controller is configured to perform the interaction with the driver based on the quiz data corresponding to the position of the vehicle received through the receiver when the amount that the steering wheel is manipulated exceeds a threshold value, even though the on state of the cruise control switch does not exceed the threshold time.

4. The apparatus for preventing passive task-related fatigue of a driver according to claim 1, wherein the receiver periodically provides position information of the vehicle to the server, under control of the controller.

5. The apparatus for preventing passive task-related fatigue of a driver according to claim 1, wherein the controller is configured to control the sheet vibrator to vibrate the sheet when the answer from the driver is the wrong answer.

6. A method for preventing passive task-related fatigue of a driver, the method comprising:
  detecting, by a cruise control monitor, an on state of a cruise control switch mounted in a vehicle;
  determining, by a controller, whether the on state of the cruise control switch exceeds a threshold time;
  receiving, by a receiver, quiz data corresponding to a position of the vehicle from a server under control of the controller when the on state of the cruise control switch exceeds the threshold time; and
  performing, by the controller, an interaction with the driver based on the quiz data corresponding to the position of the vehicle received through the receiver.

7. The method for preventing passive task-related fatigue of a driver according to claim 6, wherein the receiving of the quiz data includes transmitting position information relating to the vehicle to the server.

8. A method for preventing passive task-related fatigue of a driver, the method comprising:
  detecting, by a cruise control monitor, an on state of a cruise control switch mounted in a vehicle;
  determining, by a controller, whether the on state of the cruise control switch exceeds a threshold time;
  monitoring, by a steering wheel monitor, an amount that a steering wheel of the vehicle is manipulated;
  receiving, by a receiver, quiz data corresponding to a position of the vehicle from a server under control of the controller when the amount that the steering wheel is manipulated exceeds a threshold value while the on state of the cruise control switch does not exceed the threshold time; and
  performing, by the controller, an interaction with the driver based on the quiz data corresponding to the position of the vehicle received through the receiver.

9. The method for preventing passive task-related fatigue of a driver according to claim 8, wherein the receiving of the quiz data includes transmitting position information of the vehicle to the server.

* * * * *